United States Patent [19]

Neupert et al.

[11] Patent Number: 5,302,518
[45] Date of Patent: Apr. 12, 1994

[54] PROCESS FOR THE BIOCATALYTIC, CORRECT CHAIN FOLDING OF DENATURED RECOMBINANT FUSION PROTEINS

[75] Inventors: Walter Neupert, Germering; Franz-Ulrich Hartl, Unterschleissheim, both of Fed. Rep. of Germany

[73] Assignee: Hoechst Aktiengesellschaft, Frankfurt am Main, Fed. Rep. of Germany

[21] Appl. No.: 892,495

[22] Filed: Jun. 3, 1992

Related U.S. Application Data

[63] Continuation of Ser. No. 563,189, Aug. 6, 1990, abandoned.

[30] Foreign Application Priority Data

Aug. 8, 1989 [DE] Fed. Rep. of Germany ....... 3926103

[51] Int. Cl.⁵ .................. C07K 3/00; C07K 15/00; A61K 37/02; C12P 21/06
[52] U.S. Cl. .................................. 435/69.1; 435/69.3; 435/69.4; 435/69.52; 435/69.6; 530/402; 530/351; 530/397; 530/344
[58] Field of Search ............ 435/69.1, 69.3, 69.4, 435/69.52, 69.6; 530/402, 351, 397, 344

[56] References Cited

U.S. PATENT DOCUMENTS 4,873,312 10/1989 Arakawa .............................. 530/351

OTHER PUBLICATIONS

Nature (1988), vol. 332, pp. 776-777 (Pelham).
Science (Jul., 1989), Flynn et al., vol. 245, pp. 385-390.
Nature (1989, Feb.), Cheng et al., vol. 337, pp. 620-625.
Cell (1988), Eilers et al., vol. 52, pp. 481-483.
Molecular and Cellular Biology (1988), McMullin et al. vol. 8 (1), pp. 371-380.
Hemmingsen et al., Nature, 333, 330-334 (1988).
Reading et al., Nature, 337, 655-659 (1989).
Phillips et al., Nature, 344, 882-884 (1990).
Phelham, Cell, 46, 959-961 (1986).
Landry et al., Biological Abstract No. 36801, J. Biol. Chem., 264, 9090-9093 (1989).
Sheffield et al., Biological Abstract No. 59769, J. Biol. Chem., 265, 11069-11076 (1990).
Search Report.
R. Hendrix, "Purification and Properties of groE, a Host Protein Involved in Bacteriophage Assembly," J. Mol. Biol. 129, 375-392 (1979).

*Primary Examiner*—Robert J. Hill, Jr.
*Assistant Examiner*—Gian P. Wang
*Attorney, Agent, or Firm*—Finnegan, Henderson Farabow, Garrett & Dunner

[57] ABSTRACT

Denatured recombinant fusion proteins are correctly folded in the presence of a heat shock protein which acts according to the functional principle of the bacterial GroEL or of the equivalent mitochondrial component Hsp60, and of ATP. After cleaving off the foreign sequence, biologically and medically interesting proteins are obtained in the correct conformation.

5 Claims, No Drawings

PROCESS FOR THE BIOCATALYTIC, CORRECT CHAIN FOLDING OF DENATURED RECOMBINANT FUSION PROTEINS

This application is a continuation of application Ser. No. 07/563,189, filed Aug. 6, 1990, now abandoned.

BACKGROUND OF THE INVENTION

The complete information for the chain folding which is present in the functionally active state of a protein is contained in the amino acid sequence of the protein. This statement has been proved experimentally by the fact that correct refolding of artificially unfolded proteins has been demonstrated in vitro, even if only in selected cases (Anfinsen, C.B., Science 181: 223-230, 1973). However, there are very many gaps in the understanding of the process of protein folding, in particular of complex proteins with multiple domains or several subunits, (Jänicke, R., Biophys. Struct. Mech. 8: 231-256, 1982) and no substantial progress has been achieved in this field in recent years. The study of protein folding in vivo has been neglected completely since it has been presumed that, in principle, proteins fold in a spontaneous self assembly process even under physiological conditions (Creighton, T., in "Proteins", Freeman and Company, New York, 1984). However, this notion is most probably wrong. Many proteins which attain their functional conformation in from seconds to a few minutes after synthesis in vivo cannot be refolded in vitro after unfolding under various denaturing conditions. Recently there have been more and more findings which have led to the hypothesis that the conformation of protein chains is physiologically influenced by specific components, essentially heat shock proteins (Pelham, H., Nature 332: 776-777, 1988). Heat shock proteins are proteins which are present in the cells of organisms and are formed to a larger extent when the cells are subjected to particular forms of stress such as, for example, heat stress.

One protein component which catalyzes the correct chain folding of unfolded or newly synthesized polypeptides in vivo and in vitro has already been identified and functionally characterized This component is the heat shock protein GroEL or Hsp60 which occurs in bacteria and mitochondria. There is 60% identity of the amino acid sequences of GroEL in Escherichia coli and Hsp60 in mitochondria (Hemmingsen, S.M. Woolford, C., van der Vies, S.M. Tilly, K., Dennis, D.T., Georgopoulos, C.P. Hendrix, R.W. and Ellis, R.J., Nature 333: 330-334, 1988; Reading, D.S. Hallberg, R.L., Myers, A.M., Nature 337: 655-659, 1989). The components are present as virtually identical oligomeric complexes of 14 subunits with molecular weights of about 58,000 dalton each. Artificially unfolded or nascent proteins bind to the surface of the GroEL or Hsp60 complex. There is no specificity for bacterial or mitochondrial proteins in this case. The chain folding takes place on GroEL or Hsp60 in a reaction dependent on the hydrolysis of ATP (=adenosine triphosphate). The involvement in this process of a further component associated with the GroEL or Hsp60 complex cannot be ruled out. In the absence of ATP, for example the murine enzyme dihydrofolate reductase binds to Hsp60 in the form of an unfolded highly protease-sensitive polypeptide chain. ATP addition leads to a substantial increase in dihydrofolate reductase activity, which is initially still associated on the surface of Hsp60, and there is subsequent release of the enzyme which then is in its enzymatically active conformation. This reaction can take place inside the mitochondria at a protein concentration of about 30 to 50 g of protein/100 ml. However, it is in principle possible with isolated Hsp60 in vitro in the same way. Elimination of the Hsp60 function in a conditional yeast mutant leads to failure of mitochondrial proteins to assemble to supramolecular complexes (Cheng, M.Y., Hartl, F.U., Martin, J., Pollock, R.A., Kalousek, F., Neupert, W., Hallberg, E.M., Hallberg, R.L., and Horwich, A.L., Nature 337: 620-625, 1989).

GroEL and Hsp60 are soluble, relatively insensitive to nonspecific proteases such as proteinase K and can easily be isolated in substantial amounts from *E. coli* and the like. A method of isolation for GroEL is described, for example, in the reference Hendrix, R.W., J. Mol. Biol. 129: 375-392 (1979) GroEL is named gp groE therein. The protein gp groE is synonymous with the protein GroEL.

In the case of the isolation of Hsp60 from mitochondria, an extract which has been prepared in 0.3 % digitonin, 100 mM NaCl, 30 mM tris (=tris(hydroxymethyl)aminomethane) at pH 7.4 provides the protein Hsp60 in a good yield and sufficient purity in two purification steps by ammonium sulfate precipitation (35 to 50% saturation) and Q- ®Sepharose chromatography; Q-Sepharose is a basic ion exchanger based on agarose from Pharmacia LKB GmbH, Freiburg (Federal Republic of Germany).

SUMMARY OF THE INVENTION

It has now been found that denatured recombinant fusion proteins can also be correctly folded in the presence of heat shock proteins which act according to the functional principle of the bacterial GroEL or of the equivalent mitochondrial Hsp60; the heat shock proteins function as biocatalysts in this case.

The invention therefore relates to a process for the biocatalytic, correct chain folding of denatured recombinant fusion proteins, which comprises bringing the denatured recombinant fusion proteins into contact under normal folding conditions with a heat shock protein which acts according to the functional principle of the bacterial GroEL or of the equivalent mitochondrial Hsp60, and with ATP.

In fusion proteins, the amino acid sequences of the chimeric partners carry no information for mutual induction of folding of the individual components to give the native structure. It is therefore very surprising that fusion proteins, which are often composed of a microbial and a eukaryotic protein, can be folded with an appropriate heat shock protein into a protein whose different chimeric partners are covalently bonded in their natural structure. The protein moiety of actual interest can then be liberated from this by specific proteolysis or, if an acid-labile cleavage site has been introduced beforehand, by acid hydrolysis.

In this way, proteins of biological and medical interest can be obtained in the correct, functionally active, conformation in an advantageous and relatively simple way.

DETAILED DESCRIPTION OF THE INVENTION

Recombinant fusion proteins are prepared by genetic engineering methods. The fused portion must contain at least one amino acid. The upper limit for the number of amino acid residues in the fused portion can vary within a wide range; it is preferably about 400.

The genetically engineered preparation of peptides and proteins by the expression of the cloned genes in bacteria (usually in the form of a fusion to foreign sequences such as β-galactosidase) often results in the production of so-called inclusion bodies in which the corresponding fusion protein is present as an insoluble functionally inactive aggregate The (fusion) protein can normally be converted from this state, into a soluble form only by denaturing conditions. In this case, the (fusion) protein is completely or at least partially unfolded by artificial means. In a somewhat broader sense, denatured recombinant fusion proteins are in this context understood to be fusion proteins which are not or wrongly folded or else completely or partially unfolded by artificial means.

The denaturing of the initially insoluble and functionally inactive recombinant fusion proteins which have been obtained by the genetic engineering is carried out by customary methods by the action of denaturing agents in aqueous solution, for example by means of 6 to 8 M urea in a tris or glycine buffer at pH about 6 to 9. If the fusion protein contains disulfide linkages a reagent containing SH groups, such as, for example, mercaptoethanol or dithiothreitol is (also) necessary for unfolding, namely in an amount corresponding to at least about 2 SH groups per disulfide linkage.

The denaturing mixture (now containing the correspondingly unfolded and dissolved fusion protein) is then normally diluted such that the fusion protein concentration is preferably about 0.01 to 0.5 mg/ml (determined by the Lowry method); in some circumstances, higher concentrations (up to about 100 mg/ml) may also be appropriate or possible in the specific individual case.

The invention thus begins with the addition of an appropriate heat shock protein and of ATP.

Heat shock proteins which may be used are, in principle, all those acting according to the functional principle of the bacterial GroEL or of the equivalent mitochondrial Hsp60; GroEL and Hsp60, in particular Hsp60, are preferred. It is of course also possible to use more than one heat shock protein at the same time, but this in general does not produce any advantages.

Furthermore, it is not necessary to employ the particular heat shock protein in pure form either; on the contrary, the use in the form of an enriched extract is also suitable.

The molar ratio of fusion protein to be folded and biocatalyst for the correct chain folding (heat shock protein) can vary within wide limits; a ratio of about (10 to 100):1 is preferred.

The concentration of ATP (which is preferably used in the form of $Mg^{2+}$ ATP) can likewise vary within relatively wide limits; it is preferably about 1 to 50 mM, in particular about 2 to 10 mM.

In contrast, the pH range for the biocatalysis according to the invention is less broad; it is about 6 to 8. The pH is adjusted in a customary manner, for example by means of a tris or glycine buffer at a concentration of about 10 to 150 mM, the presence of about 50 to 200 mM NaCl or KCl also being advantageous.

The temperature for the correct chain folding is between about 15° and 30° C. as a rule.

Concentrations of denaturing reagents from the denaturing reaction which are not too high, such as, for example, up to about 0.8 M urea or up to about 0.6 M guanidinium hydrochloride, do not, in general, disturb correct folding.

The folding mixture is then worked up in a customary manner, and the fusion protein with the correct folding of the two chimeric constituents is, as a rule, cleaved by proteolysis or acidolysis in order to obtain the desired protein.

The invention will now be illustrated in more detail by the following examples.

EXAMPLES a) Dihydrofolate reductase-Fo-ATPase fusion protein

A fusion protein, which has been prepared by recombinant genetic engineering, between murine dihydrofolate reductase and the amino-terminal sequence (residues 1–66) of subunit 9 of the mitochondrial $FoF_1$-ATPase is denatured in 6 M urea, 30 mM tris-HCl, pH 7.4 (protein concentration 0.3 mg/ml).

Control reaction: after addition of 10 μl of this solution to 290 μl of 2 mM ATP, 2 mM $MgCl_2$, 100 mM NaCl, 30 mM tris-HCl, pH 7.4, and incubation at 25° C. for 20 min, the dihydrofolate reductase portion of the protein remains incompletely folded and does not attain the enzymatically active conformation.

Addition of 10 μg/ml isolated Hsp60 to the same mixture produces the enzymatically active conformation of dihydrofolate reductase with a yield of 50–70% after incubation at 25° C. for 5 min. The yield is measured via the specific activity of the fusion protein which is present as a soluble monomer after the reaction (purified by gel filtration on ®Superose 6, i.e. a molecular sieve of cross-linked agarose from Pharmacia LKB GmbH, Freiburg) and is 92 % of native dihydrofolate reductase. After the foreign sequence has been cleaved off by the specific processing peptidase of the mitochondria, the full specific activity is attained (see Example b).

b) Authentic dihydrofolate reductase (comparison)

As mixture (a) but using authentic dihydrofolate reductase as a substrate. The yield of the protein present in the enzymatically active conformation (98% of the specific activity which can be attained) is 60–80%. Dihydrofolate reductase without foreign sequences coupled to it by recombinant genetic engineering exhibits a certain tendency toward spontaneous refolding. However, in the control mixture the yield of correctly folded enzyme was only 30% under the experimental conditions used. (Dihydrofolate reductase does not contain any S-S linkages).

c) Interleukin-2-β-galactosidase fusion protein

A fusion protein, expressed in *E. coli*, between interleukin-2 and the 400 amino-terminal residues of *E. coli* β-galactosidase is dissolved out of inclusion bodies at a protein concentration of 0.2 mg/ml in 8 M urea/50 mM glycine buffer, pH 7.2. Molar equivalents of mercaptoethanol are added corresponding to the number of SH groups. The dissolved fusion protein (100 μg) is diluted 10-fold in 20 μg portions in each case in a mixture containing 5 μg/ml Hsp60 in 50 mM glycine buffer, pH 7.2. The folding reaction is started by addition of 2 mM $Mg^{2+}$ ATP and carried out at 25° C. for 15 min. Subsequently, the interleukin-2 is liberated from the fusion protein by cleavage of an acid-labile linkage(-aspartic acid-proline-) and purified by preparative HPLC separation. The retention time of the product folded in vitro was identical to that of an interleukin-2 standard. The fragment patterns after trypsin proteolysis of the folding product and of the standard likewise corresponded to each other. The specific activity as determined by a cytotoxicity test on CTLJK cells (=CytoToxic Lymphatic cells designated JK) was 9800 U/mg of protein (standard 10000 U/mg; protein determination according to Lowry). The yield of the folding reaction was 58%. It was not possible to liberate interleukin-2 from the control reaction without addition of Hsp60.

We claim:

1. A process for the biocatalytic, correct chain folding of denatured recombinant fusion proteins comprising:

contacting a fluid sample having denatured recombinant fusion proteins at a temperature from about 15° C. to about 30° C. and a pH of about 6 to about 8 with a heat shock protein selected from the group consisting of bacterial GroEL, the equivalent mitochondrial component Hsp60, and a mixture thereof, and ATP wherein ATP is employed in a concentration of about 1 to about 50 mM.

2. The process as claimed in claim 1, wherein the concentration of the denatured recombinant fusion protein is adjusted from about 0.01 to about 0.5 mg/ml.

3. The process as claimed in claim 1, wherein the heat shock protein employed is an enriched extract.

4. The process as claimed in claim 1, wherein the molar ratio of fusion protein to heat shock protein is adjusted from about 10:1 to about 100:1.

5. The process as claimed in claim 1, wherein ATP is employed in a concentration of about 2 to about 10 mM.

* * * * *